United States Patent
Ryaby et al.

[11] Patent Number: 5,626,554
[45] Date of Patent: May 6, 1997

[54] GEL CONTAINMENT STRUCTURE

[75] Inventors: John P. Ryaby, Essex Fells; Roger J. Talish, Fairfield, both of N.J.; Joan M. McCabe, White Plains, N.Y.

[73] Assignee: Exogen, Inc., Piscataway, N.J.

[21] Appl. No.: 391,109

[22] Filed: Feb. 21, 1995

[51] Int. Cl.⁶ ............................................. A61B 17/56
[52] U.S. Cl. ............................................. 601/2
[58] Field of Search ............ 128/660.01, 662.03–662.06, 128/663.01; 601/2–4; 607/51, 97, 108–111

[56] References Cited

U.S. PATENT DOCUMENTS

| | | |
|---|---|---|
| 3,499,437 | 3/1970 | Balamuth . |
| 4,530,360 | 7/1985 | Duarte . |
| 4,556,066 | 12/1985 | Semrow ............... 128/662.03 |
| 4,708,127 | 11/1987 | Abdelghani . |
| 4,787,070 | 11/1988 | Suzuki et al. ............. 367/140 |
| 4,867,169 | 9/1989 | Machida et al. ........... 128/662.03 |
| 4,936,303 | 6/1990 | Detwiler et al. ........... 607/97 |
| 5,003,965 | 4/1991 | Talish et al. . |
| 5,076,279 | 12/1991 | Arenson et al. ............ 128/662.03 X |
| 5,134,999 | 8/1992 | Osipov ................. 128/662.03 X |
| 5,186,162 | 2/1993 | Talish et al. . |
| 5,211,160 | 5/1993 | Talish et al. . |
| 5,259,384 | 11/1993 | Kaufman et al. . |
| 5,309,898 | 5/1994 | Kaufman et al. . |
| 5,327,890 | 7/1994 | Matura et al. ............ 601/2 X |

FOREIGN PATENT DOCUMENTS

| | | |
|---|---|---|
| 47359 | 3/1987 | Japan . |
| 269159 | 10/1993 | Japan . |

*Primary Examiner*—Francis Jaworski
*Attorney, Agent, or Firm*—Dilworth & Barrese

[57] ABSTRACT

This invention relates to apparatus and methods for providing and using a gel containment structure with an ultrasonic delivery system. The apparatus includes a special bladder, pad or other enclosure means for positioning adjacent the transmitting surface so that the coupling gel is retained adjacent the transmitting surface. The method for delivering ultrasonic energy includes enclosing coupling gel at the transmitting surface, positioning the enclosed coupling gel against the skin or other external location corresponding to the internal injury, and directing ultrasonic waves emitted at the transmitting surface through the enclosed conducting gel to the skin location corresponding to the internal injury.

33 Claims, 3 Drawing Sheets

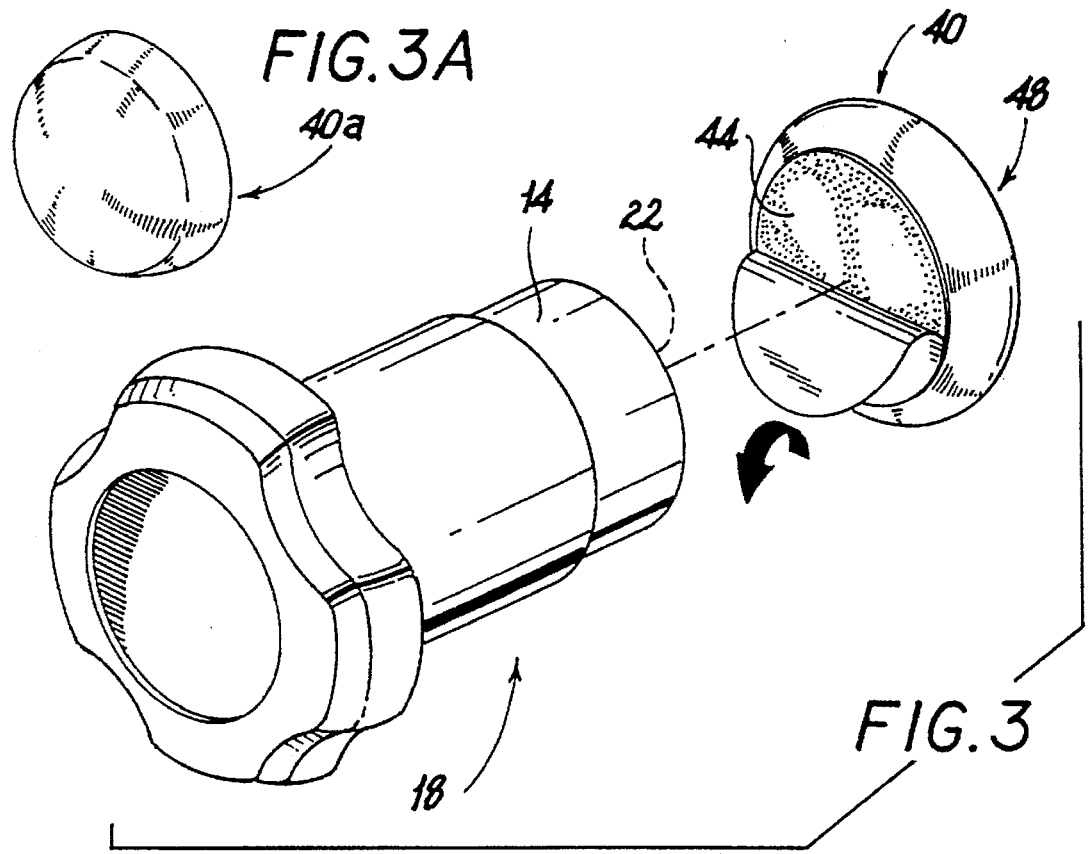
FIG. 3A
FIG. 3
FIG. 3B
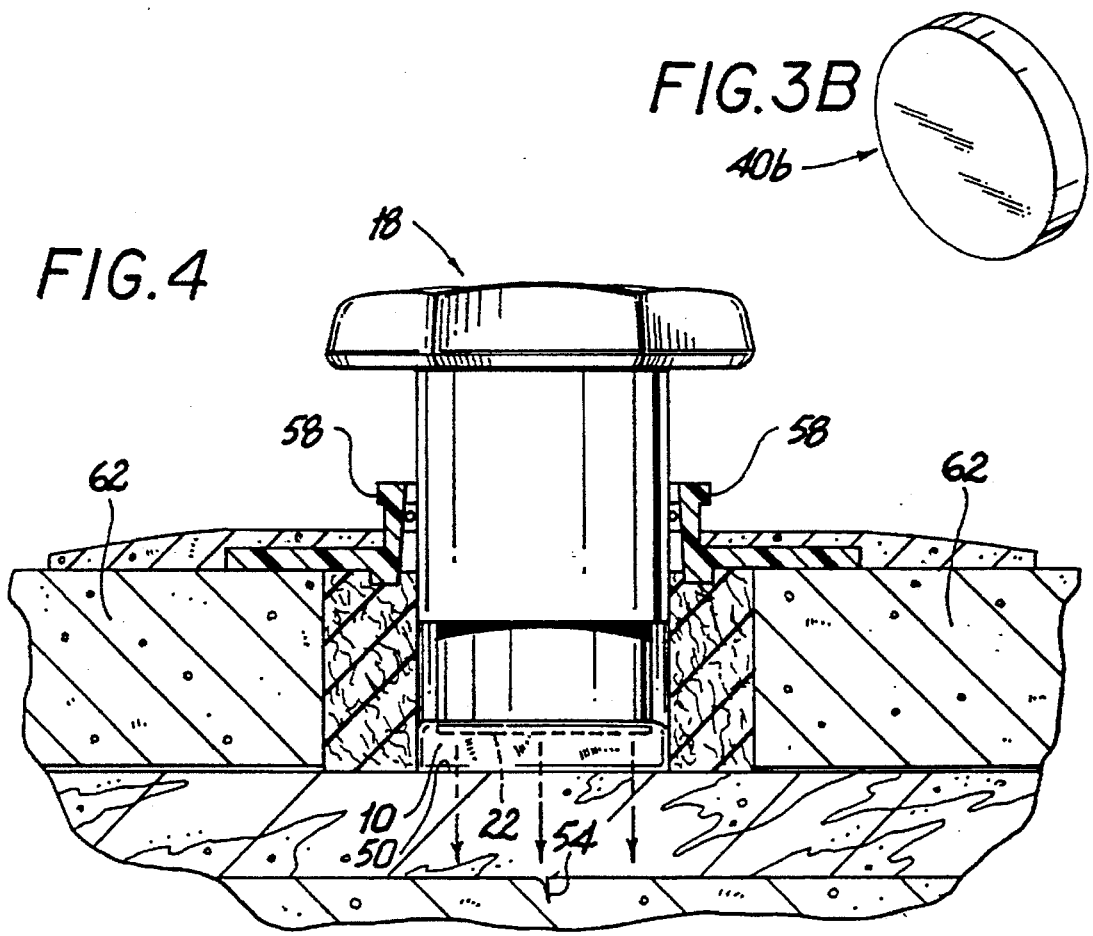
FIG. 4

1

GEL CONTAINMENT STRUCTURE

BACKGROUND OF THE INVENTION

1. Field of the Invention

This invention relates to therapeutically treating and/or evaluating musculoskeletal injuries by ultrasound and, more particularly, to a gel containment structure.

2. Description of Related Art

The use of ultrasound to therapeutically treat and evaluate bone injuries is known. Application of ultrasound of appropriate parameters in suitable dosages at a proper external location adjacent a bone injury accelerates natural healing with few or no adverse side effects. For patients with reduced healing capacity, such as many elderly persons, ultrasonic therapy may promote healing of bone injuries that would otherwise require prosthetic replacement or leave the patient permanently disabled.

U.S. Pat. No. 4,530,360 to Duane ("Duarte") describes a basic therapeutic technique and apparatus for applying ultrasonic pulses from an operative surface placed on the skin at a location adjacent a bone injury. The "operative surface" of an ultrasonic delivery system, as that term is used in this application, is the exposed tangible surface of the system that transmits the ultrasonic pulses into the surroundings. For some systems the operative surface may be the transducer surface itself, while in others it may be a surface layer on top of the transducer surface. Duarte gives a range of RF signals for creating the ultrasound, ultrasound power density levels, a range of duration for each ultrasonic pulse, and a range of ultrasonic pulse frequencies. The length of daily treatment is described.

U.S. Pat. Nos. 5,003,965 and 5,186,162 both to Talish and Lifshey ("Talish '965" and "Talish '162," respectively) describe an ultrasonic delivery system where the RF generator and operative surface are both part of a modular applicator unit that is placed adjacent the skin location. The signals controlling the duration of ultrasonic pulses and the pulse repetition frequency are generated apart from the applicator unit. Talish '965 and Talish '162 also describes fixture apparatus for attaching the applicator unit so that the operative surface is adjacent the skin location. In Talish '965 and Talish '162, the skin is surrounded by a cast, while in U.S. Pat. No. 5,211,160 to Talish and Lifshey ("Talish '160") fixture apparatus is described for mounting on uncovered body parts (i.e., without a cast or other medical wrapping). Talish '160 also describes various improvements to the applicator unit.

It is known in the art that ultrasonic pulses attenuate rapidly in gases, such as air, and that, consequently, propagation of the ultrasonic pulses from the operative surface to the injury must be through a medium comprised of solids and liquids in order for the ultrasonic pulses to be efficiently transmitted. Since it is often not possible to press the operative surface completely flush against the external skin location corresponding to an internal injury, ultrasonically conductive coupling gel (hereinafter referred to as "coupling gel") is used between the operative surface and the skin to ensure a continuous contact. In fact, more recent systems implement a small zone between the operative surface and the skin for the coupling gel, thereby excluding any direct contact between the operative surface and the skin. Talish '162 describes such a system.

Duarte, Talish '965, Talish '162 and Talish '160 are all incorporated into this application by reference.

While the systems described in these references, and others, disclose the underlying therapeutic method and apparatus to one skilled in the art, they do not disclose a way of completely containing the coupling gel to the region between the skin and the operative surface. Previously, the coupling gel was often simply placed onto the operative surface. When the operative surface and the skin were brought together for treatment, the gel squeezed out into neighboring regions. This is especially undesirable when the ultrasonic treatment is delivered through an opening in a medical wrapping, such as a cast, because the gel soils the adjacent interior portions of medical wrapping.

Other systems contain the gel, but imperfectly. For example, in the system described in Talish '162, the gel is injected into a small zone created by a circumferential lip formation between the operative surface and the skin. Even in this system, however, gel squeezes between the lip and the skin when excess gel is injected to ensure the zone is completely filled.

It is therefore an objective of this invention to provide apparatus for containing the coupling gel substantially to the interface between the operative surface and the skin.

SUMMARY OF THE INVENTION

To achieve these objectives, the present invention includes an ultrasonic delivery system for therapeutic use having a base, an ultrasonic generation means mounted to the base, the ultrasonic generation means including an exposed operative surface positionable adjacent a skin location, and enclosure means for sealingly retaining coupling gel substantially adjacent the operative surface.

The enclosure means may be used in conjunction with most any type of ultrasonic delivery system, including a module system, or a more traditional handheld system.

The enclosure means may take on many designs which are, in part at least, a function of the delivery system make-up. Generally, many ultrasonic delivery systems have a telescoping portion with the operative surface exposed at the end face, thereby enabling the operative surface to be positioned adjacent the skin. This includes the hand-held system of Duarte, as well as modular systems, such as Talish '162. For such systems, the enclosure means may be a non-porous bladder with an elastic opening that stretches over the end face of the telescoping portion, including the operative surface. The body of the bladder may also be made of an elastic or rubberized material, which may stretch over the end face of the telescoping portion, including the operative surface. Alternatively, an ultrasonic or chemically activatable porous bladder may be used to contain the coupling gel. In these embodiments the material of the bladder is substantially non-porous until activated either by ultrasound or by chemical application such as, for example, by rubbing the bladder with alcohol. Once activated, the pores open and exude the ultrasonically conductive coupling gel.

It is also envisioned that a preformed disk of ultrasonically conductive polyurethane may be positioned intermediate the operative surface of the ultrasonic generation means and the skin to provide a conductive conduit for the generated ultrasound energy. Alternatively, a polyurethane bladder can be used having ultrasonically conductive coupling gel disposed therein. In these embodiments, the disk or bladder can be independently positioned in operative position between the skin and the ultrasonic generation means.

The enclosure means may also be a cap, similar in nature to a lens cap. The cap fits over the end face of the telescoping portion, including the operative surface, so that the cap band frictionally engages the telescoping portion. The cap band may be comprised of a flexible and resilient material, such as plastic. The cap cover may also be flexible and resilient, or may be supple, such as a thin plastic.

The enclosure means may also be a closed pouch or pad that may be fastened to the end face of the telescoping portion, covering the operative surface with a portion of the pouch or pad.

The present invention also includes a method for delivering ultrasonic therapy to an internal injury from an ultrasonic delivery system having a base housing an ultrasonic generation means with an exposed operative surface, comprising the steps of sealingly enclosing coupling gel substantially adjacent the operative surface, positioning the enclosed coupling gel adjacent an external location corresponding to the internal injury, and directing ultrasonic waves emitted at the operative surface through the enclosed coupling gel to the external location corresponding to the internal injury. Preferably, a thin film of coupling gel, mineral oil, glycerine, water or other ultrasonically conductive material is spread over the outer surface of the bladder to enhance performance of the transducer.

This method of delivering ultrasonic therapy may include disposing coupling gel on the operative surface, and stretching an opening of a bladder to receive the operative surface within the bladder. The gel may be applied to the operative surface and then the bladder is placed over the gel and the operating surface. Alternatively, the gel may be disposed in the bladder and the bladder with the enclosed gel is then placed over the operative surface. At least part of the surface of the bladder opposite the operative surface is then placed adjacent a skin location corresponding to an internal injury.

This method of delivering ultrasonic therapy may also include adhering a portion of the surface area of a closed bladder containing conductive gel to at least part of the operative surface. At least part of the surface of the bladder opposite the operative surface is then placed adjacent a skin location corresponding to an internal injury.

BRIEF DESCRIPTION OF THE DRAWINGS

The preferred embodiments of the invention are described below with reference to the drawings, which are described as follows:

FIG. 3 is a perspective view of a conductive gel pad with a portion attached to the front end of a telescoping portion of an ultrasonic treatment module;

FIG. 3A is a perspective view of a self-contained gel bladder configured for positioning between the operative surface of the ultrasonic treatment module and the skin;

FIG. 3B is a perspective view of a self-contained ultrasonically conductive polyurethane disk configured for positioning between the operative surface of the ultrasonic treatment module and the skin;

FIG. 4 is a side-view in cross-section of a module type ultrasonic delivery system adjacent a skin location with a gel bladder retaining the conductive gel between the operative surface and the skin location.

DETAILED DESCRIPTION OF THE PREFERRED EMBODIMENT

Figure 1:
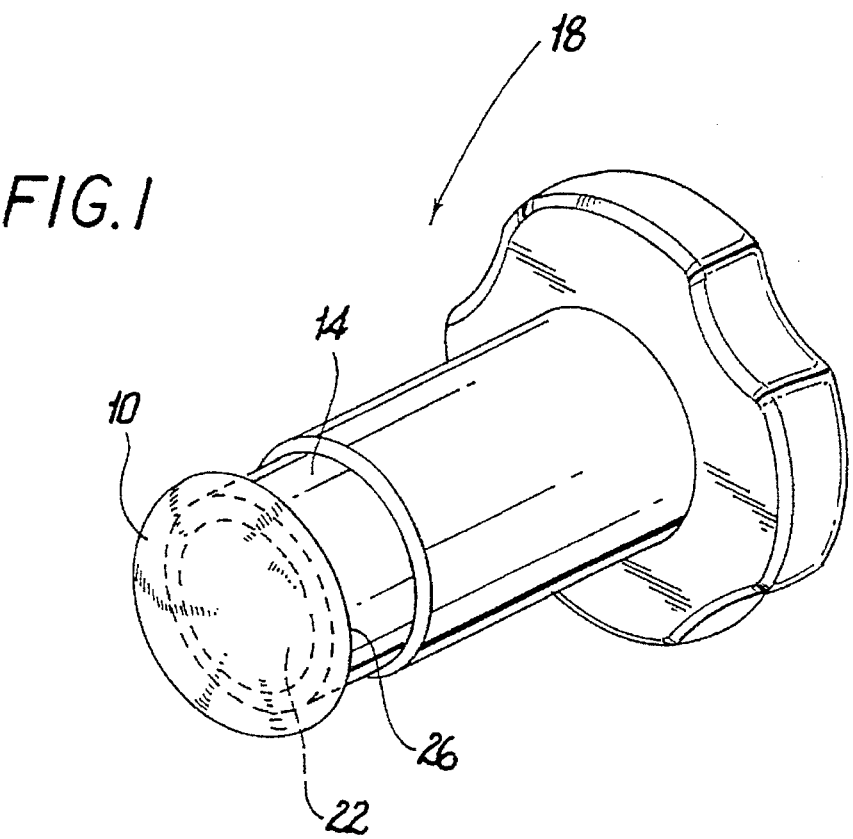
FIG. 1 is a perspective view of a conductive gel bladder enveloping the front end of a telescoping portion of an ultrasonic treatment module.
Figure 2:
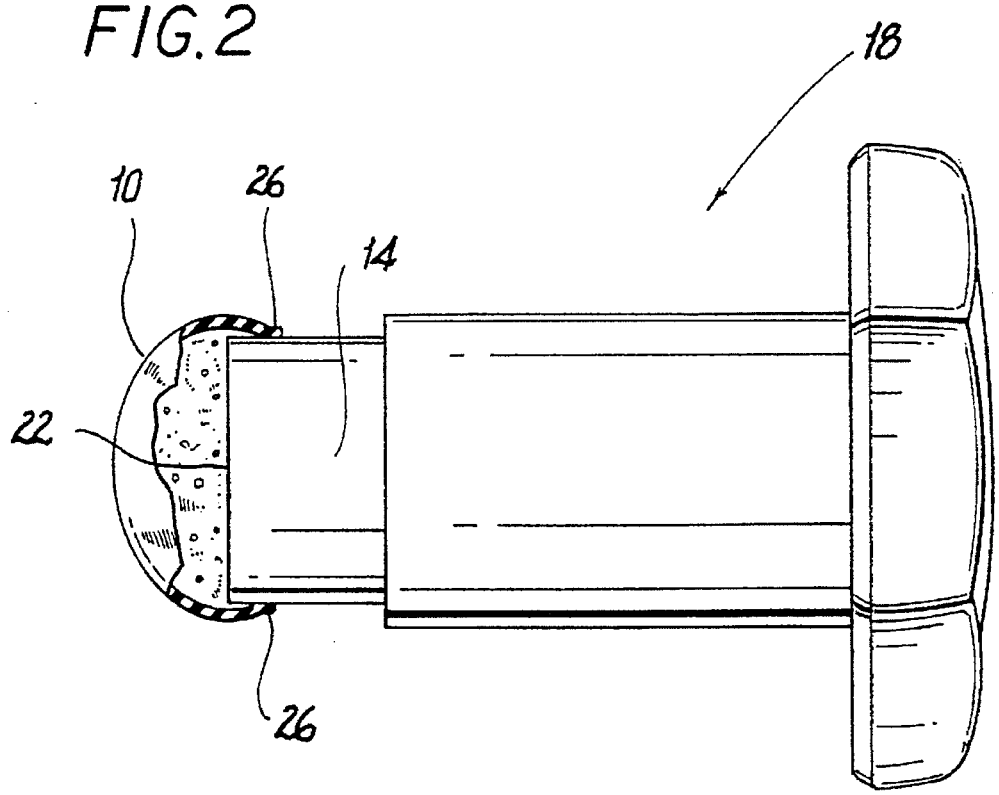
FIG. 2 is a side-view in cross-section of a conductive gel bladder enveloping the front end of a telescoping portion of an ultrasonic treatment module.

Referring to FIGS. 1 and 2, an ultrasonically conductive gel bladder 10 of the present invention is shown enveloping the front telescoping portion 14 of an ultrasonic treatment module 18. In particular, the gel bladder 10 contains ultrasonically conductive gel and covers the operative surface 22 of the module 18, which is substantially co-planar with the front end of the telescoping portion 14.

The gel bladder 10 is constructed of a thin supple plastic, or equivalent material, and completely envelops the front end of the telescoping portion 14, including the operative surface 22. Alternatively, the gel bladder 10 may be constructed of an ultrasound conductive rubberized material which may stretch over the front end of the telescoping portion 14. This is better suited for systems such as that shown in the Talish '162 patent, where the front end of the telescoping portion 14 has a small circumferential lip that extends slightly beyond the operative surface 22 in an axial direction.

The gel bladder 10 has opening 26 through which the front end of the telescoping portion 14 is inserted. The perimeter of the opening 26 has an elastic property which, in its unstretched state, is smaller than the perimeter of the front end of the telescoping portion 14. Thus, the opening 26 must be stretched to insert the front end of the telescoping portion 14 within the gel bladder 10. Once inserted, the stretched opening 26 contracts partially to contact the telescoping portion 14, but still remains in a stretched state. Friction created between the stretched opening 26 and the telescoping portion 14 resists the gel bladder 10 from being pulled off the telescoping portion 14.

The elastic property of the opening 26 may be an elastic band fastened adjacent the opening 26 of the gel bladder 10. This is more suited to a gel bladder 10 constructed of supple plastic, for example. If the body of the gel bladder 10 is constructed of an ultrasonically conductive rubberized material, for example, then the opening 26 will be inherently elastic, although reinforcing layers of the rubberized material would also normally be built around the opening 26.

The gel bladder 10 may be constructed of either a porous or non-porous material depending upon the desired application. Preferably, where a porous material is used, for example, PTFE filter material, the pores are expandable upon the application of a chemical activator such as, for example, alcohol. This permits the pores to extrude conductive material only after being contacted with the chemical activator.

The perimeter of opening 26 is elastic in the preferred embodiment. Non-elastic configurations and materials, such as a drawstring with a fastening mechanism, or an ultrasound conductive adhesive layer adjacent the opening, may be substituted. The perimeter of the opening 26, may also be made of material that shrinks when heat is applied, so that the opening 26 contracts to sealingly engage the telescoping portion 14. The whole gel bladder 10 itself may be made of material that shrinks when heat is applied.

FIG. 3 shows an alternative embodiment of the present invention in the form of a gel pad 40. The gel pad 40 is a sealed (or closable) unit enclosing ultrasonically conductive gel therein and having a back portion 44 that adheres to the front end of the telescoping portion 14, including the operative surface 22, covering the operative surface 22. The ultrasonically conductive adherent may be a gummed surface layered onto the back portion 44, with a thin, removable film covering it. The front portion 48 of the gel pad 40 is a supple material, such as a thin plastic, that can assume the contour of the skin location that it is pressed against during ultrasonic therapy.

FIGS. 3a and 3b show additional alternative embodiments of structures for use with transducers such as gel pads and ultrasonically conductive disks, respectively of the present invention. The gel pad 40a of FIG. 3a is similar in structure to the gel pad 40 of FIG. 3, except that it does not have an adhering back portion. The disk 40b of FIG. 3b is a self-contained ultrasonically conductive polyurethane disk, again without an adhering layer for adhering to an operative surface. The structures 40a, 40b of FIGS. 3a and 3b, respectively, are configured to be most adaptable to a module-type ultrasonic delivery system, described below. Specifically, these structures 40a, 40b are configured to be received within the aperture of a fixture that is fastened adjacent the skin location, and is pressed between the skin and the operative surface of the ultrasonic delivery system when the module engages the fixture.

FIG. 4 shows the gel bladder of FIGS. 1 and 2 being used during ultrasonic therapy. The module 18 is brought adjacent a skin location 50 corresponding to an injury 54, so that the front surface of the gel bladder 10 (i.e., the surface opposite the operative surface 22) engages the skin location 50. The gel inside the gel bladder 10 and the surface of the gel bladder 10 adjacent the skin location 50 form a continuous, non-gaseous coupling between the operative surface 22 and the skin location 50, while containing the gel substantially to the region between the operative surface 22 and the skin location 50.

In a module system, the module 18 normally interfaces with, and is held in place adjacent to the skin location 50 by a fixture 58 fastened adjacent the skin location 50. As shown in FIG. 4, such module systems may also be adapted to skin covered with a cast 62 or other medical wrapping.

As noted, ultrasonic waves attenuate rapidly in gases, so the ultrasonically conductive coupling gel in the gel bladder 10 and the front portion of the gel bladder 10 that engages the skin location 50 provide a continuous, non-gaseous pathway for ultrasonic waves between the operative surface 22 and the bone injury 54. The gel bladder 10 substantially confines the gel to the region between the operative surface 22 and the skin location 50, where it is needed. Without the gel bladder 10, much of the gel 55 squeezes outside the region between the operative surface 22 and the skin location 50, where it creates an undesireably contamination of the cast 62 or other medical wrapping.

Depending on the material composition of the gel bladder 10, it may be necessary to apply a thin layer of ultrasound conductive coupling gel or other ultrasonically conductive material on the front surface of the gel bladder 10 that engages the skin location 50. This thin layer of material eliminates any remaining minute gaps between the gel bladder 10 and the skin location 50, while the amount squeezed into adjacent areas, if any, is insignificant.

Figure 5:
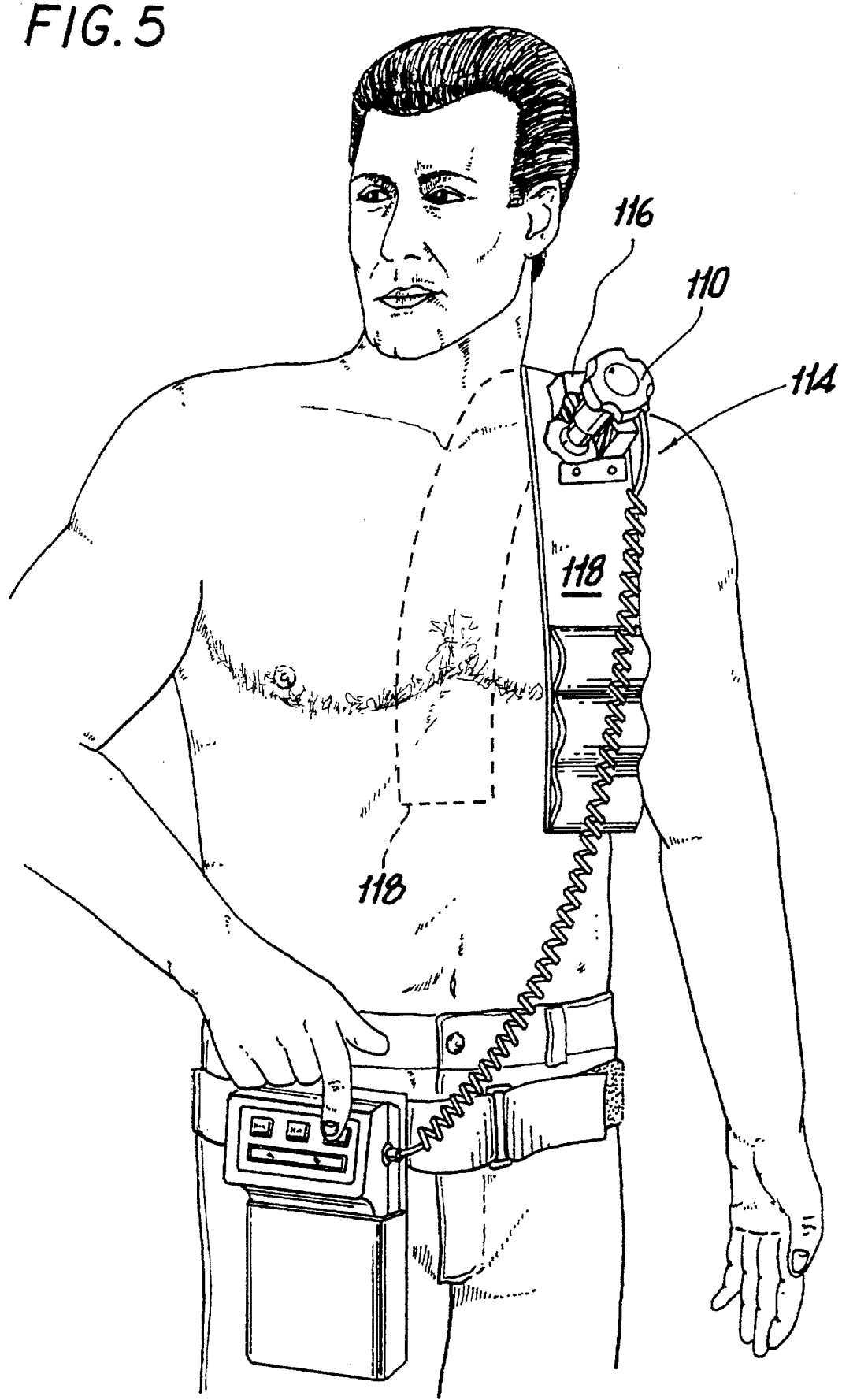
FIG. 5 is a perspective view of a portable module type ultrasonic delivery system including an ultrasonically conductive gel bladder configured for use in clavicle fractures.

Referring to FIG. 5, a preferred embodiment of the present invention is shown in application to a patient with a clavicle fracture. Clavicle fractures present a particularly difficult problem in efficiently applying ultrasound to a situs adjacent a fracture. This is caused by the uneven topography of the skin and musculoskeletal structure in the clavicle region and the difficulty in maintaining the operative surface of the transducer housing in the necessary orientation for effective treatment. As described and shown above, the gel bladder is sufficiently elastic to effectively conform to the shape of the skin topography adjacent a fracture site. Pressure applied normally to the gel bladder and the skin location, such as that provided by the module system of FIG. 4, aids the conformation. The bladder may, advantageously, be coated with an ultrasonically conductive material such as, e.g., ultrasonically conductive coupling gel or other ultrasonically conducting material. For a clavicle injury, the transducer housing 110 is held in position by a harness 114 including a mounting portion 116 and a draped depending weighted belt 118. Belt 118 is draped over the chest and back of the patient with the gel bladder/transducer housing positioned operatively adjacent the clavicle fracture site. In this manner the gel bladder serves to efficiently conduct the ultrasound energy to the fracture site while the harness 114 helps to maintain the transducer housing in a uniform position for treatment.

It will be understood that various modifications can be made to the various embodiments of the present invention herein disclosed without departing from its spirit and scope. For example, various sizes and shapes of the gel containment means are contemplated, as well as various construction materials. Also, various modifications may be made in the configuration of the parts. For example, when a gel bladder with an opening is used, the opening may be taped to the telescoping portion of the ultrasonic treatment module, thereby containing the gel. Also, a gel supply tube may be configured to lie along the telescoping portion of the transducer housing and interface with the interior of the gel bladder when the gel bladder is positioned over the telescoping portion. This would allow additional gel to be supplied to the bladder during treatment, if needed. Similarly, various modifications may be made to the above-described sequence of the invention in method without departing from its spirit and scope. For example, when a closed pouch contains the conductive gel, part of the pouch may be adhered to the operative surface before the gel is inserted in the pouch and the pouch is closed. Therefore the above description should not be construed as limiting the invention but merely as presenting preferred embodiments of the invention. Those skilled in the art will envision other modifications within the scope and spirit of the present invention as defined by the claims presented below.

What is claimed is:

1. Ultrasonic delivery system for therapeutic use having a base;

ultrasonic generation means mounted to the base, the ultrasonic generation means including an exposed operative surface positionable adjacent a skin location; a coupling gel and enclosure means for sealingly retaining the coupling gel substantially adjacent the operative surface and for isolating the operative surface from a skin location, the enclosure means being attached to the ultrasonic generation means immediately adjacent the outer periphery of the operative surface.

2. Ultrasonic delivery system as in claim 1 wherein the enclosure means is a sheath.

3. Ultrasonic delivery system as in claim 1 wherein the enclosure means is a bladder with an opening for enveloping the operative surface of the ultrasonic generation means.

4. Ultrasonic delivery system as in claim 3 wherein the bladder is formed of a non-porous material.

5. Ultrasonic delivery system for therapeutic use having:
a base;
ultrasonic generation means mounted to the base, the ultrasonic generation means including an exposed operative surface positionable adjacent a skin location; and a bladder for sealingly retaining coupling gel substantially adjacent the operative surface, the bladder having an opening for enveloping the operative surface of the ultrasonic delivery system, wherein the bladder is formed of a material having a plurality of pores which expand in response to a chemical activator to cause the material with the expanded pores to be porous to coupling gel.

6. Ultrasonic delivery system as in claim 1 wherein the ultrasonic generation means further includes a telescoping portion having the operative surface; and the enclosure means is a cap for covering the operative surface of the telescoping portion of the ultrasonic generation means.

7. Ultrasonic delivery system of claim 1 wherein the enclosure means is a closed bladder with a means for attaching a portion of the exterior surface of the bladder adjacent the operative surface.

8. Ultrasonic delivery system of claim 1 wherein the enclosure means is comprised at least in part of material selected from the group consisting of rubber, polyurethane elastic and supple plastics.

9. Ultrasonic delivery system for therapeutic use having a base defining a forward planar region;

ultrasonic generation means within the base having an exposed operative surface positionable adjacent a skin location, the exposed operative surface housed adjacent and parallel to the forward planar region; a conductive gel and a bladder for sealingly retaining the conductive gel substantially adjacent the operative surface and for isolating the operative surface from a skin location, the bladder being attached to the ultrasonic generation means immediately adjacent the outer periphery of the operative surface.

10. Ultrasonic delivery system as in claim 9 wherein the bladder is formed of a non-porous material.

11. Ultrasonic delivery system for therapeutic use having:

a base defining a forward planar region;

ultrasonic generation means within the base having an exposed operative surface positionable adjacent a skin location, the exposed operative surface housed adjacent and parallel to the forward planar region; and a bladder for retaining conductive gel substantially adjacent the operative surface wherein the bladder is formed of a material having a plurality of pores which expand in response to a chemical activator to cause the material with the expanded pores to be porous to conductive gel.

12. Ultrasonic delivery system as in claim 9 wherein the bladder has an opening for receiving the distal end of the base, whereby the bladder envelops the operative surface.

13. Ultrasonic delivery system as in claim 12 wherein the perimeter of the opening of the bladder is expandable for receiving the distal end of the base.

14. Ultrasonic delivery system as in claim 12 wherein the bladder is elastic and has a surface area smaller than the forward planar region, whereby the bladder stretches to receive the distal end of the base and envelop the operative surface.

15. Ultrasonic delivery system for therapeutic use having a base with a telescoping portion, one end of the telescoping portion defining a forward planar region;

ultrasonic generation means within the base having an exposed operative surface positionable adjacent a skin location, the exposed operative surface housed adjacent and parallel to the forward planar region of the telescoping portion; a conductive gel and a closed bladder containing the conductive gel coupled substantially adjacent the operative surface and for isolating the operative surface from a skin location, the bladder being attached to the ultrasonic generation means immediately adjacent the outer periphery of the operative surface.

16. Ultrasonic delivery system as in claim 15 wherein a portion of the exterior surface of the bladder includes means for removably fastening the bladder to the operative surface.

17. Ultrasonic delivery system as in claim 15 wherein a portion of the exterior surface of the bladder includes adherent for adhering the bladder to the operative surface.

18. Ultrasonic delivery system for therapeutic use having an ultrasonic treatment module with a telescoping portion, the distal end of the telescoping portion defining a forward planar region;

ultrasonic generation means housed within the ultrasonic treatment module and including an exposed operative surface approximately co-planar with the forward planar region of the telescoping portion;

a positionable fixture for retaining and aligning the ultrasonic treatment module with the operative surface adjacent a skin location; a coupling gel, a bladder with an expandable opening for receiving the distal end of the telescoping portion and sealingly retaining the coupling gel substantially between the operative surface and the skin location and for isolating the operative surface from a skin location, the bladder being attached to the ultrasonic generation means immediately adjacent the outer periphery of the operative surface.

19. Ultrasonic delivery system as in claim 18 wherein said bladder is formed of a non-porous material.

20. Ultrasonic delivery system for therapeutic use having:

an ultrasonic treatment module with a telescoping portion, the distal end of the telescoping portion defining a forward planar region;

ultrasonic generation means housed within the ultrasonic treatment module and including an exposed operative surface approximately co-planar with the forward planar region of the telescoping portion;

a positionable fixture for retaining and aligning the ultrasonic treatment module with the operative surface adjacent a skin location;

a bladder with an expandable opening for receiving the distal end of the telescoping portion and sealingly retaining coupling gel substantially between the operative surface and the skin location, wherein said bladder is formed of a material having a plurality of pores which expand in response to a chemical activator to cause the material with the expanded pores to be porous to coupling gel.

21. Ultrasonic delivery system for therapeutic use comprising an ultrasonic treatment module with a telescoping portion, the distal end of the telescoping portion defining a forward planar region;

ultrasonic generation means housed within the ultrasonic treatment module and including an exposed operative surface approximately co-planar with the forward planar region of the telescoping portion;

a positionable fixture for retaining and aligning the ultrasonic treatment module with the operative surface adjacent a skin location;

a non-porous closed bladder containing coupling gel with an ultrasonically conductive adherent on a portion of its external surface that adheres to the operative surface for retaining coupling gel substantially between the operative surface and the skin location.

22. Method for delivering ultrasonic therapy to an internal injury from an ultrasonic delivery system having a base housing an ultrasonic generation means and an exposed operative surface, comprising the steps of:

a) sealingly enclosing coupling gel substantially adjacent the operative surface to isolate the operative surface from a skin location by attaching an enclosure member to the ultrasonic generation means immediately adjacent the outer periphery of the operative surface;

b) positioning the enclosed coupling gel adjacent an external location corresponding to the internal injury; and c) directing ultrasonic waves emitted at the operative surface through the enclosed coupling gel to the external location corresponding to the internal injury.

23. Method as in claim 22, wherein the step of sealingly enclosing coupling gel substantially adjacent the operative surface includes the step of disposing coupling gel on the operative surface.

24. Method as in claim 22, wherein the step of sealingly enclosing coupling gel substantially adjacent the operative surface includes disposing a bladder over the operative surface.

25. Method as in claim 22, wherein the step of sealingly enclosing coupling gel substantially adjacent the operative surface includes disposing coupling gel on the operative surface and stretching an opening of a bladder and receiving the operative surface within the bladder.

26. Method as in claim 25, wherein the step of positioning the enclosed coupling gel adjacent an external location corresponding to the internal injury includes the step of positioning at least part of the external surface of the bladder opposite the operative surface adjacent a skin location corresponding to an internal injury.

27. Method as in claim 22, wherein the step of sealingly enclosing coupling gel substantially adjacent the operative surface includes the step of adhering a portion of the surface area of a closed bladder containing coupling gel to at least part of the operative surface.

28. Method as in claim 27, wherein the step of positioning the enclosed coupling gel adjacent an external location corresponding to the internal injury includes the step of positioning at least part of the external surface of the bladder opposite the operative surface adjacent a skin location corresponding to an internal injury.

29. Method as in claim 22 wherein said external location corresponding to the internal injury comprises a human clavicle region.

30. Method as in claim 22, wherein the step of sealingly enclosing coupling gel substantially adjacent the operative surface includes disposing a non-porous bladder over the operative surface.

31. Method as in claim 22, wherein the step of sealingly enclosing coupling gel substantially adjacent the operative surface includes disposing a bladder formed of a material having a plurality of pores which expand in response to a chemical activator to cause the material with the expanded pores to be porous to the coupling gel over the operative surface.

32. Ultrasonic delivery system for therapeutic use having:

a base mountable adjacent a skin location;

ultrasonic generation means mounted to the base, the ultrasonic generation means including an exposed operative surface positionable adjacent a skin location;

a coupling gel and enclosure means for sealingly retaining the coupling gel substantially adjacent the operative surface and for isolating the operative surface from a skin location, the enclosure means being attached to the ultrasonic generation means immediately adjacent the outer periphery of the operative surface.

33. Ultrasonic delivery system of claim 32 further comprising:

means for removably mounting the base adjacent the skin location for allowing the ultrasonic delivery system to be portable.

* * * * *